(12) United States Patent
Wilson

(10) Patent No.: US 7,972,839 B2
(45) Date of Patent: Jul. 5, 2011

(54) AEROBIC COMPOST TEA MAKING DEVICE AND METHOD

(76) Inventor: Timothy James Wilson, Westbridge (CA)

( * ) Notice: Subject to any disclaimer, the term of this patent is extended or adjusted under 35 U.S.C. 154(b) by 384 days.

(21) Appl. No.: 12/355,822

(22) Filed: Jan. 19, 2009

(65) Prior Publication Data

US 2009/0191613 A1 Jul. 30, 2009

Related U.S. Application Data

(60) Provisional application No. 61/023,804, filed on Jan. 25, 2008.

(51) Int. Cl.
*C12M 1/00* (2006.01)
(52) U.S. Cl. ............... 435/290.1; 435/290.2; 435/290.3; 435/290.4
(58) Field of Classification Search ..... 435/290.1–290.4
See application file for complete search history.

(56) References Cited

U.S. PATENT DOCUMENTS

| 4,687,645 | A * | 8/1987 | Harvey | 435/290.3 |
| 7,727,758 | B1 * | 6/2010 | Posthuma | 435/290.1 |
| 2002/0081717 | A1 * | 6/2002 | Morrison | 435/290.1 |
| 2002/0164781 | A1 * | 11/2002 | Alms et al. | 435/290.1 |

* cited by examiner

*Primary Examiner* — Michael A Marcheschi
*Assistant Examiner* — Jameson Q Ma

(57) ABSTRACT

The device and method invented provides a unique means to extract and multiply, by the millions, beneficial aerobic microbes found in compost and vermicompost to be applied to soil and plants in liquid form. Compared to many compost tea making devices being sold, the invented device is truly simple and can be dismantled and cleaned in under twenty minutes. Most of the parts are not glued and can be pulled apart. The device and method uses air pumps alone to actually circulate the water and can be used with or without a mesh extractor. This is achieved by the insertion of an air diffuser into the piping used, which infuses the water with oxygen while circulating the water, into either, an extractor containing compost or a body of water containing compost. Concurrently additional diffusers infuse the body of water with oxygen.

6 Claims, 3 Drawing Sheets

AEROBIC COMPOST TEA MAKING DEVICE AND METHOD

This application claim benefit of priority to U.S. provisional Patent Application Ser. No. 61/023,804, filed Jan. 25, 2008, the contents of which are incorporated herein by reference in its entirety.

BACKGROUND FOR DEVICE

At the interface of roots of plants and soil there exists a region which can be abundant with beneficial microbes comprising basically of bacteria, archaea, fungi, protozoa (amoebae, flagellates, ciliates) and yeasts which live in a symbiotic food relationship with each other. Without going into great detail concerning the roles of all parties, that symbiotic food relationship or microbial nutrient cycle has great benefit to the soil and plants. Certain bacteria and archaea receive nutrition from substances released from the roots of plants, those bacteria and archaea are in turn consumed by protozoa which release substances, in the form of waste, which provide nutrients to the roots of plants, thus creating a nutrient cycle. There is also evidence that applications of compost tea may help suppress plant pathogens. The inventor has done considerable microscopic research on soil and compost microbes. The device and method invented implements the creation of a functional microbial nutrient cycling consortia to be applied to soil and plants, thus initiating or boosting the beneficial microbes at the root/soil interface.

The word compost shall be used henceforth herein to mean compost, vermicompost or both. The operating principle and design of the invented device may be applied to virtually any size of water vessel with adjustment of pipe and diffuser size and of air pump capacity. There are various compost tea making devices being sold, which operate by blowing bubbles into the body of water or use a water pump to circulate the body of water. This device differs entirely by actively circulating the body of water through pipes with use of air alone while concurrently infusing the water with oxygen by way of diffusers secured within the pipes and diffusers submerged in the water. There are several configurations of the device which the user may employ. One configuration has compost placed in free suspension in the body of water with circulating water being returned so as to break the surface tension of the body of water. Another configuration uses a mesh extractor container into which compost is placed and into which the circulating water empties so as to provide the option of compost containment. A third configuration allows the continued use of the mesh extractor container with one or more diffusers placed into it with the compost with the circulating water bypassing the mesh extractor container.

The invented device and method has several benefits when compared to other compost tea devices presently on the market. Other devices for sale and known to the inventor which are air operated simply blow air into the body of water or blow air into an extractor container or both without actuating circulation. Although some of these have claims of actively circulating the water, the inventor has observed no way to measure such circulation. The invented device and method invented easily demonstrates and measures circulation.

Other devices for sale and known to the inventor which do circulate the water do so with water pumps which potentially damage the microbes being extracted with each pass through the pump impellers and the effects on raising the dissolved oxygen are limited compared to those of an air pump.

Judging from the stated recommendations for using many other compost tea devices on the market, the average recommended operational times are limited to twenty-four to thirty-six hours. One might conclude that this time limitation is based on the device's inability to maintain the minimum dissolved oxygen content of 6 PPM (parts per million) necessary to sustain aerobic microbial life. The device and method invented has demonstrated the ability to maintain a dissolved oxygen level of 8.8 PPM to 9.8 PPM in the 50 gallon device configuration operated in excess of 48 hours when using 4% compost, 0.75% molasses, 0.063% fish hydrolysate and 0.25% kelp meal in water with a temperature of approximately 19 degrees Centigrade and having a beginning TDS (total dissolved solids) of 21 PPM. The inventor feels this demonstrates the superior efficiency of the device to raise and maintain the level of dissolved oxygen.

The inventor has sought from the onset of research and development to create a compost tea making device and method which is affordable by homeowners and small farm owners and because of the design simplicity he will accomplish this.

BRIEF DESCRIPTION OF THE ATTACHED DRAWINGS

DETAILED DESCRIPTION OF DEVICE AND METHOD

Figure 3:
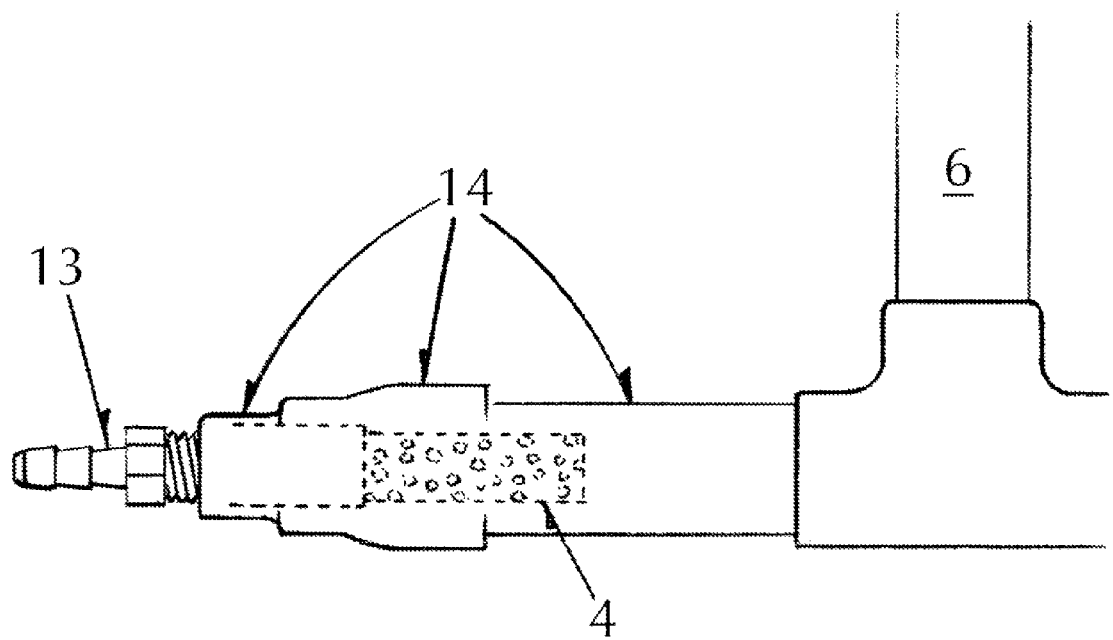
FIG. 3 shows an enlargement of a typical method employed to secure an air diffuser inside the pipe comprising the device.

To explain the design and operation more clearly I will describe the device configured for use with approximately 50 gallons (US), as it is depicted in the accompanying diagrams. Several lengths of pipe are connected by angled pipe junctions so one pipe, herein called the riser pipe, 6 in the diagrams, is on the vertical plane and several short lengths are configured at right angles to each other on the horizontal plane. The short lengths of pipe on the horizontal plane are resting on the bottom of a vessel 10 with over 50 gallon holding capacity. They are submerged in water and configured to have two open ends, herein called water intake openings, 5 in the diagrams, at opposing positions within the space of the vessel and an end proximal to the riser pipe 6 into which an air diffuser, 4 in the diagrams, is inserted and secured by means of pipe fittings and glue, exemplified by FIG. 3, 14. The riser pipe 6 is attached to the pipes on the horizontal plane by way of a Tee shaped pipe junction and rises so as to be several inches above the surface 9 of the water. Connected to the top of the riser pipe 6 is a ninety degree pipe junction, connected to a short length of pipe which is connected to a second ninety degree pipe junction, herein called the return nozzle, 7 in the diagrams, pointed down so as to terminate, suspended two to three inches above and at an approximate right angle to the surface 9 of the water. The device is provided air and energy by an air pump, 1 in the diagrams, with a minimum capacity of one cubic foot per minute of air per fifteen gallons of water. The air is provided to two diffusers by way of air tubing, 2 in the diagrams, connected to the air pump 1 and connected by a Tee shaped junction to distribute the air to the two diffusers. One diffuser, herein called diffuser 'A', 4, as previously described is inserted into pipe which is secured to the Tee junction proximal to the base of the riser pipe 6, diffuser 'A' 4, being located so as to terminate recessed from the base of the riser pipe 6. The air tubing 2 is connected to diffuser 'A' 4 by a pipe fitting, FIG. 3, 13, barbed on the connection end and threaded on the other end so as to be attached to the pipe fittings, FIG. 3, 14, securing diffuser 'A' 4 inside the pipe. The other diffuser, herein called diffuser 'B', 8 in the diagrams, is located so as to sit horizontally, proximal to the bottom of the vessel 10. The air tube 2 is connected to diffuser 'B' 8 by way of a pipe fitting. Connected to the air tubing and in between diffuser 'A' 4 and diffuser 'B' 8 is an air flow control valve, 3 in the diagrams, to adjust the dispersal of air to each diffuser. Of note is that diffuser 'A' 4 is smaller in size so as to fit in the pipe but diffuser 'B' 8 is larger to provide maximum infusion of air into the water. Both diffusers, in this case, are of a quality grade, machined from a solid block of glass bonded silica and capable of efficient infusion of water with oxygen.

OPERATION OF DEVICE

For ease in understanding the diagrams the following numbers refer to the various components;

1—air pump; 2—air tubing; 3—air control valve; 4—diffuser 'A'; 5—water intake openings; 6—riser pipe; 7—return nozzle; 8—diffuser 'B'; 9—water surface/level; 10—water vessel; (FIG. 2) 11—down pipe; 12—mesh extractor bag; (FIG. 3) 13—barbed fitting; 14—arrangement of several pipe fittings.

Figure 1:
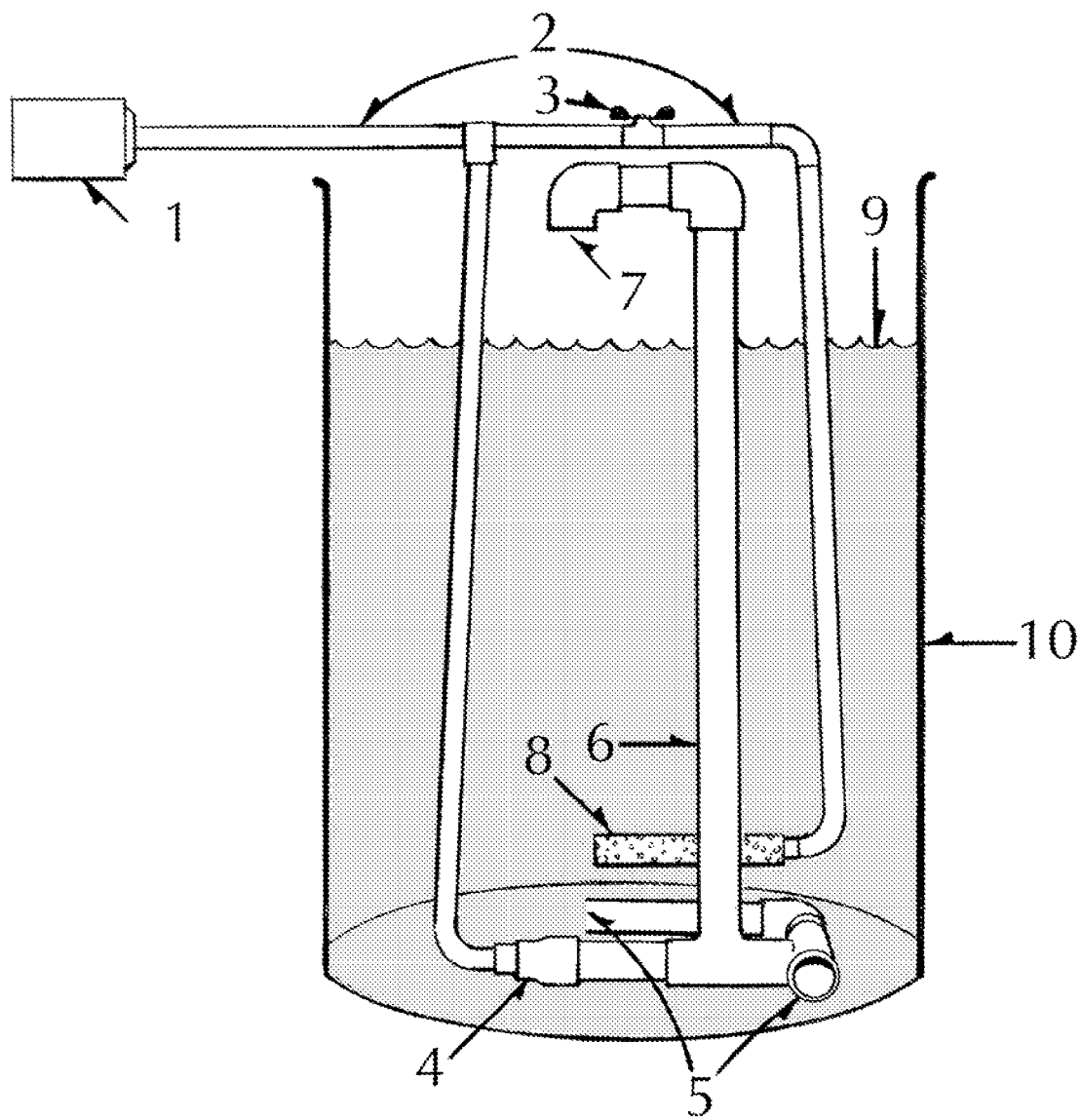
FIG. 1 shows the device as configured for use with a 50 (US) gallon vessel without use of an extractor container.

Configuration 1: FIG. 1

When the vessel is filled with water to the appropriate level 9, the device is operated, when configured for using compost in free suspension in the body of water, by providing power to the air pump 1. The air control valve 3, in the air tubing 2, is adjusted to observe water coming from the return nozzle 7 and bubbles rising from diffuser 'B' 8. To ensure sufficient flow a container approximately 1 liter (1 quart (US), held under the return nozzle, should take less than three seconds to fill and the air control valve 3 can be adjusted to fine tune the water flow to this rate. This flow of water is taking place as diffuser 'A' 4 powered by the air pump 1 causes water to be drawn from the two water intake openings 5 and pushed up the riser pipe 6 and out the return nozzle 7. With this action the water is being infused with oxygen at two interfaces. One interface is at diffuser 'A' 4 itself because water is injected with oxygen as it is pushed past the diffuser. The second interface of oxygen infusion occurs as the water flows from the return nozzle 7 with sufficient force to break the surface 9 tension barrier, allowing the release of carbon dioxide and the absorption of oxygen. This is commonly referred to as the gas exchange process. This action pushes the oxygenated water into the body of water further raising the dissolved oxygen content of the water. Because the water intake openings 5 are located at opposing sides at the bottom of the vessel, a current-like flow is created and maintained so any still areas of water are highly unlikely. Further infusion of air and absorption of oxygen by the body of water is provided by the air passing through diffuser 'B' 8. Oxygen is absorbed by the interface of the tiny bubbles created on the way to the surface 9 and the surface tension barrier is broken by the bubble turbulence, allowing the release of carbon dioxide and the absorption of oxygen. By these methods the device is able to raise and maintain the dissolved oxygen content of the body of water in a very efficient yet simple manner. Testing has shown that the device raises the dissolved oxygen of water an average of 3 PPM above its natural state, when the temperature of the water is between 18 and 21 degrees Centigrade (65 to 70 Fahrenheit) and the water has a TDS (totally dissolved solids) of 21 PPM.

Maintaining a reasonably high rate of dissolved oxygen in the body of water is essential to the device's efficiency for extracting and multiplying the beneficial aerobic microbes, consisting of; archaea, bacteria, fungal hyphae, flagellates, amoebae, some ciliates, yeast cells and yeast fungal hyphae.

Once the device is operating a measured amount of compost is added to the body of water along with measured amounts of the appropriate microbial feed such as black strap molasses, fish hydrolysate and kelp meal. The compost becomes mixed into the circulating body of water and is broken up into smaller particles. The circulating action, the force of impact with the water's surface along with the air from diffusers provides sufficient agitation to break the microbes loose from their binding spots in the compost. The continuous flow provides a more homogenous dispersal of oxygen and microbes avoiding still water areas where potential undesired microbial life may develop. Once free swimming or bound to smaller particles, the bacteria, archaea, yeast cells and fungal hyphae graze on the feed supplied and multiply. Because of the reasonably high dissolved oxygen content of the body of water, primarily beneficial aerobic bacteria and archaea multiply rather than potentially detrimental high numbers of anaerobic microbes. As more semi-microscopic and microscopic particles are created, there are more surfaces created to which microscopic fungal hyphae can adhere. In response to the increase in the bacterial and archaeal population, protozoa begin to multiply and graze on the bacteria and archaea, increasing in numbers, at a later time period during the process, thus creating a functional microbial nutrient cycling consortia. Because of the reasonably high dissolved oxygen content of the body of water, primarily the oxygen loving protozoa, flagellates and amoebae will grow. Generally speaking, if the user wishes to have a compost tea consisting of bacteria, archaea and fungal hyphae (and yeast if present in compost) for a specific soil or plant type, the operating time will be twenty-two to twenty-four hours and if they wish to have protozoa present as well, for a nutrient cycling compost tea, the operating time will be forty-four to forty-eight hours. It should be underscored that the use of quality compost and ingredients is directly proportional to a quality compost tea.

Figure 2:
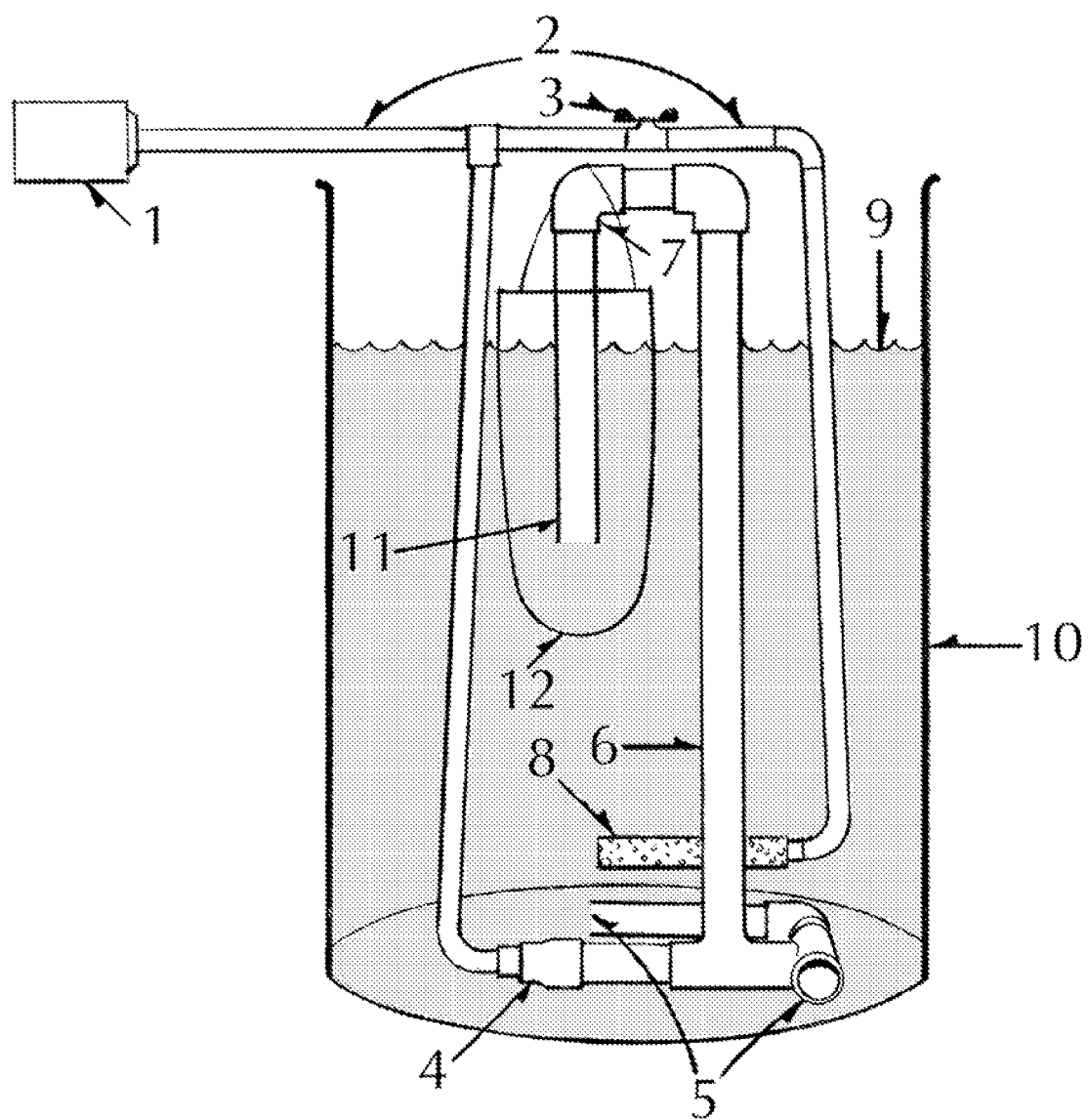
FIG. 2 shows the device as configured for use with a 50 (US) gallon vessel incorporating an extractor container.

Configuration 2: FIG. 2

The user, when operating the device, may wish to use the additional parts included to contain the compost, alternative to it being in free suspension in the body of water. The additional parts consist of a mesh extractor bag 12, with a structural ring at the top, a plastic lid with a central hole and a nylon line for suspending the bag from the return nozzle 7. There is a pipe, herein called the down pipe 11, which attaches to the return nozzle 7, passes through the hole in the plastic lid into the mesh extractor bag 12 and extends about three quarters the length of the mesh extractor bag 12, the end of the down pipe 11 being open. A measured amount of compost and solid microbial feed, like kelp meal, is placed into the mesh extractor bag 12, it is suspended by the nylon line from the return nozzle 7, the down pipe 11, placed in the mesh extractor bag 12, protruding through the hole in the lid, is inserted into the return nozzle 7, the vessel 10 is filled with water to the appropriate level 9 and the device is started by providing power to the air pump 1. The device works in similar fashion as when configured without the mesh extractor bag 12, however the difference is that the oxygenated water coming from the return nozzle 7 and the down pipe 11 agitates the compost in the mesh extractor bag 12, breaking microbes free from their binding spots and pushing them through the mesh into the body of water where they multiply as previously described. Microscopic examinations have shown that the device, configured this way, is not quite as efficient in microbial production, for nutrient cycling purposes. It is however beneficial for the exclusion of particles from the compost tea, especially important when using as a foliar application to leaves and it is effective for creating a primarily bacterial amendment for control of pathogens.

Configuration 3:

There is no diagram illustrating this configuration. A third configuration of the device provides for the continued use of the mesh extractor bag with the compost placed into it as previously described and with diffuser 'B' placed into the mesh extractor bag with the compost. Using the nylon line, the mesh extractor bag is suspended from the return nozzle pipe or from some other convenient surface. The down pipe is not used and the return nozzle is rotated to a position where the return flow of water bypasses the mesh extractor bag. In this configuration diffuser 'B' provides enough agitation upon the compost within the mesh extractor bag to break microbes free from their binding spots and push them through the mesh into the body of water where they multiply as previously described. Additionally diffuser 'B' is oxygenating the water in and surrounding the mesh extractor bag. The advantages to using this configuration is that the compost is contained, reducing particles, the water is still breaking the surface as it flows from the return nozzle, promoting dissolved oxygen content, the microbes in the body of water are not carried back into the mesh extractor bag and the initial agitation is a little less turbulent. The use of this configuration is recommended by the inventor for producing a compost tea high in fungal hyphae content.

I claim:

1. An apparatus for extracting and multiplying aerobic microbes found in compost and vermicompost consisting of:
    a vessel containing a body of water;
    an air pump;
    a vertical pipe within said vessel connected at a bottom end to one or more shorter pipes by a pipe junction, the one or more shorter pipes resting on the bottom of the vessel;
    an air diffuser secured inside said pipe junction by means of glue which is provided air from the air pump by means of a tubing;
    said vertical pipe also connected at a top end to a ninety degree pipe junction, connected to a horizontal pipe, which is further connected to a return nozzle, said return nozzle having an opening which faces the bottom of the vessel;
    a second air diffuser proximal to the bottom of the vessel which is also connected to the air pump and is capable of bubbling air when submerged in water;
    a control valve connected to said tubing and second air diffuser;
    said air pump capable of producing sufficient cubic feet per minute of air to cause water to enter an opening in the one or more shorter pipes resting on the bottom of the vessel and up the vertical pipe and out through the return nozzle.

2. A method for extracting and multiplying aerobic microbes found in compost and vermicompost comprising:
    providing an apparatus according to claim 1;
    filling the vessel with water;
    operating said air pump at a sufficient cubic feet per minute of air for said diffusers to infuse said water with dissolved oxygen while pushing said water up the vertical pipe above the surface of said water through said horizontal pipe and out of said second ninety degree pipe junction, said water being dropped out said return nozzle from a sufficient height to break the surface tension of said body of water and to actuate the absorption of oxygen by said body of water enhancing the action of gas exchange;
    and said air pump providing air to said second diffuser to which causes bubbles to rise out of said second diffuser.

3. A method for extracting and multiplying aerobic microbes found in compost and vermicompost according to claim 2, further comprising:
    placing an amount of compost or vermicompost into said water;
    placing an amount of microbial food into said water in free suspension.

4. An apparatus for extracting and multiplying aerobic microbes found in compost and vermicompost consisting of:
    a vessel containing a body of water;
    an air pump;
    a vertical pipe within said vessel connected at a bottom end to one or more shorter pipes by a pipe junction, the one or more shorter pipes resting on the bottom of the vessel;
    an air diffuser secured inside said pipe junction by means of glue which is provided air from the air pump by means of a tubing;
    said vertical pipe also connected at a top end to a ninety degree pipe junction, connected to a horizontal pipe, which is further connected to a return nozzle, said return nozzle connected to a down pipe;
    a mesh extractor bag with a plastic lid comprising a central hole and a nylon line attached to the return nozzle;
    said down pipe extending through the central hole and into said mesh extractor bag;
    a second air diffuser proximal to the bottom of the vessel which is also connected to the air pump and is capable of bubbling air when submerged in water;
    a control valve connected to said tubing and second air diffuser;
    said air pump capable of producing sufficient cubic feet per minute of air to cause water to enter an opening in the one or more shorter pipes resting on the bottom of the vessel and up the vertical pipe and out through the down pipe.

5. A method for extracting and multiplying aerobic microbes found in compost and vermicompost comprising:
    providing an apparatus according to claim 4
    filling the vessel with water;
    operating said air pump at a sufficient cubic feet per minute of air for said diffusers to infuse said water with dissolved oxygen while pushing said water up the vertical pipe above the surface of said water through said horizontal pipe and out of said second ninety degree pipe junction, said water being dropped out said return nozzle from a sufficient height to break the surface tension of said body of water and to actuate the absorption of oxygen by said body of water enhancing the action of gas exchange;
    and said air pump providing air to said second diffuser to which causes bubbles to rise out of said second diffuser.

6. A method for extracting and multiplying aerobic microbes found in compost and vermicompost according to claim 5, further comprising:
    placing an amount of compost or vermicompost into said mesh extractor bag;
    placing an amount of microbial food into said water in free suspension.

* * * * *